United States Patent [19]

Magdányi et al.

[11] 3,956,312
[45] May 11, 1976

[54] INDAZOLE-3-CARBOXYLIC ACID HYDRAZIDES AND A PROCESS FOR THE PREPARATION THEREOF

[75] Inventors: László Magdányi; Lujza Petöcz; Enikö Kiszelly; Ibolya Kosóczky; Attila Varga, all of Budapest, Hungary

[73] Assignee: Egyt Gyógyszervegyészeti Gyár, Budapest, Hungary

[22] Filed: Aug. 15, 1974

[21] Appl. No.: 497,676

[30] Foreign Application Priority Data
Aug. 16, 1973 Hungary.............................. EE 2169

[52] U.S. Cl............................. 260/310 C; 424/273
[51] Int. Cl.².......................................... C07D 231/56
[58] Field of Search ................................. 260/310 C

[56] References Cited
UNITED STATES PATENTS
3,007,938  11/1961  Kirchner....................... 260/310 C
3,705,175  12/1972  Magdanyi et al. ............. 260/310 C OTHER PUBLICATIONS
Chemical Abstracts, Vol. 79;137031m (1973).

Primary Examiner—Donald B. Moyer

[57] ABSTRACT

New compounds of the general formula (I)

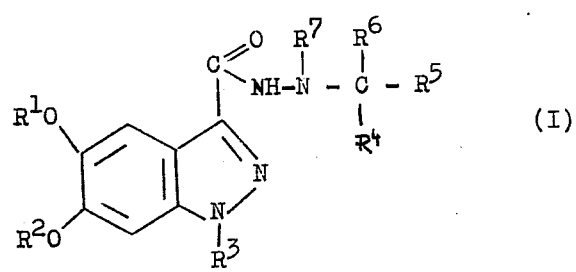

(I)

and salts thereof were prepared by reacting a compound of the general formula (II)

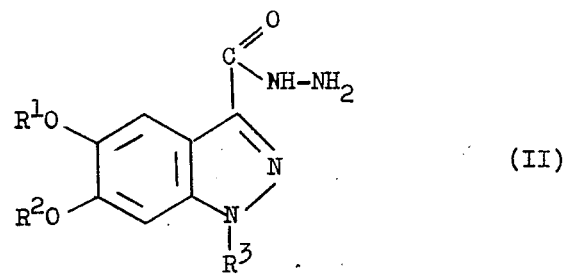

(II)

with a compound of the general formula (III) or (IV)

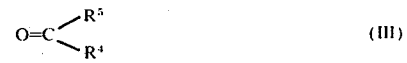

(III)

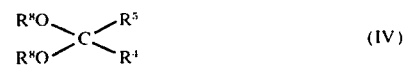

(IV)

and optionally saturating the —C=N— bond.

In the above formulae $R^1$ and $R^2$ are always the same and represent a $C_{1-4}$ alkyl group, $R^3$ stands for hydrogen, $R^4$ and $R^5$ each represent hydrogen or a straight-chained or branched $C_{1-16}$ alkyl group optionally having an unsubstituted or substituted phenyl, furyl or naphthyl substituent, wherein said substituted aryl groups may contain up to 3 alkyl, $C_{1-3}$ alkoxy, benzyloxy, nitro, amino, lower alkylamino, di-lower alkylamino, methylenedioxy, alkylmercapto, alkylsulfonyl or halogen substituents, or $R^4$ and $R^5$ may form together with the adjacent carbon atom a $C_{3-12}$ cycloalkyl or $C_{3-12}$ cycloalkylidene group, one of the methylene ring members of which being optionally replaced by an imino, lower alkylimino, or phenyl-lower alkylimino group, and $R^6$ and $R^7$ may stand for hydrogen, or $R^6$ and $R^7$ may form together a valence bond, and the $R^8$ groups may each represent hydrogen, lower alkyl or alkanoyl, or the two $R^8$ groups may form together a lower alkylene or alkanoylene group.

The compounds of the general formula (I) possess primarily gastric acid secretion inhibiting and central nervous activities, furthermore they exert favourable action on the development of certain microorganisms which can be utilized in therapy.

4 Claims, No Drawings

INDAZOLE-3-CARBOXYLIC ACID HYDRAZIDES AND A PROCESS FOR THE PREPARATION THEREOF

This invention relates to novel indazole-3-carboxylic acid hydrazides and pharmaceutical compositions containing the same, as well as to a process for the preparation thereof. The new compounds according to the invention possess primarily gastric acid secretion inhibiting and central nervous activities, and they exert favourable action on the development of certain microorganisms which can be utilized in therapy.

The new compounds according to the invention correspond to the general formula (I)

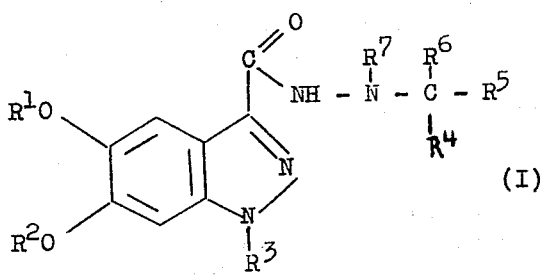

wherein $R^1$ and $R^2$ are always the same and represent a $C_{1-4}$ alkyl group, $R^3$ stands for hydrogen, $R^4$ and $R^5$ each represent hydrogen or a straight-chained or branched $C_{1-16}$ alkyl group optionally having an unsubstituted or substituted phenyl, furyl or naphthyl substituent, wherein said substituted aryl groups may contain up to 3 alkyl, $C_{1-3}$ alkoxy, benzyloxy, nitro, amino, lower alkylamino, di-lower alkylamino, methylenedioxy, alkylmercapto, alkylsulfonyl or halogen substituents, or $R^4$ and $R^5$ may form together with the adjacent carbon atom a $C_{3-12}$ cycloalkyl or $C_{3-12}$ cycloalkylidene group, one of the methylene ring members of which being optionally replaced by an imino, lower alkylimino, or phenyl-lower alkylimino group, and $R^6$ and $R^7$ may stand for hydrogen, or $R^6$ and $R^7$ may form together a valence bond.

Compounds with similar structures have so far been described only in U.S. Pat. No. 3,007,938 and J. Heterocycl. Chem. 1, 240 (1964).

The compounds of the general formula (I) can be prepared by reacting an indazole-3-carboxylic acid hydrazide of the general formula (II)

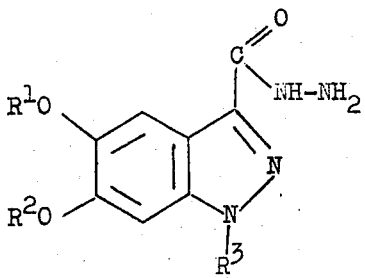

wherein $R^1$, $R^2$ and $R^3$ each have the same meanings as defined above, with an aldehyde or ketone of the general formula (III)

wherein $R^4$ and $R^5$ each have the same meanings as defined above, or with an aldehyde or ketone derivative of the general formula (IV)

wherein $R^4$ and $R^5$ each have the same meanings as defined above and the $R^8$ groups may each represent hydrogen, lower alkyl or alkanoyl, or the two $R^8$ groups may form together a lower alkylene or alkanoylene group, and, if desired, reducing any —N=C— group present in the side chain of the obtained compound to form an —NH—CH— group.

The compounds of the general formula (I) that contain centres capable of salt formation can be converted, if desired, into their acid addition salts formed with mineral or organic acids. These salts and the preparation thereof are also covered by the scope of the invention.

The compounds of the general formula (II) are reacted with the compounds of the general formulae (III) or (IV) preferably in the presence of a solvent and/or diluent. It is also preferred to use the reagents of the general formulae (III) or (IV) in excess. The reaction is carried out preferably at a temperature exceeding 20°C, most preferably at about the boiling point of the reaction medium. The excess of the reagents having the general formulae (III) or (IV) can be removed by distillation or extraction. This method can be applied to great advantage for those reagents of the general formulae (III) or (IV) wherein one of the substituents $R^4$ and $R^5$ is hydrogen, and the other represents a lower alkyl group. Such compounds are e.g. acetaldehyde, propionaldehyde, butyraldehyde, etc. With this reagents the reaction proceeds readily even without external heating. As solvent and/or diluent e.g. alcohols (such as methanol, ethanol, isomeric propanols and butanols, glycol, diethyleneglycol, propylene glycol, glycerol), mono- or polyethers of polyfunctional alcohols (e.g. methyl cellosolve, diglyme, etc.), ethers (such as diethyl ether, dibutyl ether, dioxane, tetrahydrofuran), aromatic hydrocarbons (such as benzene, toluene, xylene), furthermore acetic acid, dimethylformamide, dimethylacetamide, acetonitrile, etc., or mixtures thereof can equally be used.

One may proceed in a similar manner when using reagents of the general formula (III) or (IV) that contain lower alkyl groups as $R^4$ and $R^5$ substituents, e.g. acetone, methylethylketone or the halogenated derivatives thereof, but in this instance the reaction is preferably accelerated by heating, optionally at the boiling point of the mixture.

According to another advantageous process variant the compounds of the general formula (II) are reacted with the reagents of the general formulae (III) or (IV) in molten state (the water formed in the reaction can easily escape the melt). This reaction is carried out preferably at a temperature of 100° to 140°C. When the reagent of the general formula (III) or (IV) is used in excess, the unreacted residue is removed preferably by extraction. It is also preferable to carry out the reaction in molten state with nearly equimolar amounts of the reagents; the molar ratio of the compound of the general formula (II) and the compounds of the general formulae (III) or (IV) being preferably between 1.0 and 2.0.

The compounds of the general formula (II) are reacted with the reagents of the general formulae (III) or (IV) optionally in the presence of a mineral or organic acid. These acids promote the reaction. It is particularly preferred to perform the reaction in the presence of an acid when the reagent of the general formula (IV) contains a lower alkyl or lower alkanoyl group as $R^8$.

The subsequent optional reduction of the —C=N— group can be carried out in a hydrogenating apparatus in a lower alkanol medium, using catalytically activated hydrogen gas. For this purpose metal catalysts, e.g. nickel, palladium, cobalt, or platinum can be used. A molar equivalent of hydrogen is generally taken up within 10 to 50 hours. Thereafter the catalyst is removed by filtration, the filtrate is evaporated, and the residue is purified by recrystallization, extraction or column chromatography.

The reduction can also be carried out to advantage with a metal borohydride (such as sodium, potassium, lithium, calcium, or aluminium borohydride) in a lower alkanol or ether medium (such as dioxane, tetrahydrofuran or diethyleneglycol dimethylether), at a temperature of 0° to 100°C. In this instance the reaction takes place within 0.5 to 4 hours. When the reaction has ceased, the mixture is admixed with water, and the product is separated by filtration, extraction and/or evaporation. According to a particularly preferred method, the reduction is carried out with sodium borohydride in isopropanol medium, at about the boiling point of the mixture.

Finally, the reduction can also be performed with diborane. It is very surprising that with diborane as reducing agent solely the —N=C— bond is reduced, and the —CO— moiety of the —CO—NH—N=C— group remains unchanged, since according to the literature diborane can be used to convert —CO— groups into —$CH_2$— groups (see e.g. U.S. Pat. No. 3,678,059, describing the reduction of indazole-3-carboxylic amides into the corresponding 3-aminomethyl-indazoles). The reaction can be carried out at a temperature between −20°C and +20°C, preferably at about 0°C. As reaction medium, preferably dioxane, tetrahydrofuran, glycol dimethylether, or diethyleneglycol dimethylether is used.

According to a particularly preferred method, diborane is formed in situ in the reaction mixture itself, e.g. by the addition of boron trifluoride to sodium borohydride. In this case the reduction proceeds very quickly, usually within some minutes. When the reaction has ceased, the mixture is acidified, and the product is separated by any of the above methods.

The compounds of the general formula (I) or their salts can be converted, either alone or together with other biologically active and/or synergistic agents, into pharmaceutical compositions. These compositions may contain conventional pharmaceutical solvents, carriers, diluents and/or other auxiliary substances, and may be presented as pharmaceutical products for oral, parenteral or topical administration.

The new compounds according to the invention possess very advantageous, therapeutically valuable biological effects. Of these effects the suppression of gastric acid secretion, the spasmolytic effects, and the actions characteristic of antidepressant drugs are to be mentioned primarily. The various effects of certain compounds found to be outstandingly active are given below.

The spasmolytic effect was tested under in vivo conditions on white mice, by the carbon suspension method of Stickney. The active agents were administered intraperitoneally, and the total length of the small intestines as well as the length of the intestines filled with carbon were measured. When the carbon suspension did not reach the half of the total length of the small intestines, the result was regarded positive. The $ED_{50}$ values were calculated according to the LitchfieldWilcoxon method from the thus-transformed values. In order to evaluate the safety margin of the active agents, the acute $LD_{50}$ values were also determined on white mice in intraperitoneal administration. The observation periods in the toxicity tests were 48 hours, and the calculation was performed according to the LitchfieldWilcoxon method, also taking into consideration the perished animals. The results are listed in Table 1.

Table 1

| Compound | Compound No. | Toxicity $LD_5$ mg./kg. | Spasmolytic effect $ED_{50}$ mg./kg. | Therapeutical index $LD_{50}/ED_{50}$ |
|---|---|---|---|---|
| 5,6-dimethoxyindazole-3-carboxylic acid-isopropylhydrazide | 7 | 720 | 36 | 20.0 |
| 5,6-dimethoxyindazole-3-carb- | | | | |

Table 1-continued

| Compound | Compound No. | Toxicity $LD_5$ mg./kg. | Spasmolytic effect $ED_{50}$ mg./kg. | Therapeutical index $LD_{50}/ED_{50}$ |
|---|---|---|---|---|
| oxylic acid-cycloheptylhydrazide | 28 | 1200 | 280 | 4.3 |
| 5,6-dimethoxyindazole-3-carboxylic acid-2'-hydroxybenzylhydrazide | 32 | above 3000 | 25 | 120.0 |
| 5,6-dimethoxyindazole-3-carboxylic acid-1'-(4''-nitrophenyl)-ethylhydrazide | 35 | 5000 | 2.5 | 2000.0 |
| 5,6-dimethoxyindazole-3-carboxylic acid-2'-(3'-/3'',4''-dimethoxyphenyl/)-propylhydrazide | 37 | 2700 | 8.7 | 310.3 |
| papaverine | — | 132 | 46.0 | 2.9 |

The therapeutical indices indicate that all the compounds tested are much more favourable in spasmolytic effect than papaverine.

The inhibition of gastric acid secretion was examined on Wistar rats starved for 48 hours. The animals were operated according to Shay's method, and the substance to be tested was administered intraperitoneally. After 5 hours the animals were sacrified, and the volume of gastric juice, the amount of free hydrochloric acid, and the total acidity were determined. The results are listed in Table 2.

Table 2

| Compound | Compound No. | Dosage mg./kg. | Percentage inhibition of gastric juice | Percentage inhibition of free HCl | Percentage inhibition of total acidity |
|---|---|---|---|---|---|
| 5,6-dimethoxy-indazole-3-carboxylic acid isopropylhydrazide | 7 | 50 | 75 | 78 | 73 |
| | | 100 | 80 | 85 | 67 |
| 5,6-dimethoxy-indazole-3-carboxylic acid cycloheptylhydrazide | 28 | 50 | 46 | 47 | 38 |
| | | 100 | 47 | 63 | 36 |
| 5,6-dimethoxy-indazole-3-carboxylic acid benzylhydrazide (toxicity on mice: 2000 mg./kg. p.o.) | 30 | 50 p.o. | 36 | 50 | 39 |
| | | 100 p.o. | 48 | 76 | 63 |
| | | 25 i.p. | 13 | 33 | 20 |
| | | 100 " | 48 | 74 | 56 |
| | | 200 " | 63 | 72 | 64 |
| Xylamide* | — | 500 | 81 | 89 | 80 |
| Adiphenine** | — | 100 | 36 | 0 | 0 |

Remarks:
*Rovati, A.L. et al.: Minerva Medica 58, 3651 (1967)
**2-diethylaminoethyl-diphenylacetate hydrochloride (McCol, J.D. et al.: Arch. Intern. Pharmacodyn. 141, 181 /1963/)

The antiulcer activity of 5,6-dimethoxyindazole-3-carboxylic acid-benzylhydrazide was determined on rats. The results are listed in Table 3.

Table 3

| Dosage mg./kg. | Percentage inhibition related to the controls averages according to the ulcer diameters (mm.) | | | | occurrence of ulcer | ulcer index |
|---|---|---|---|---|---|---|
| | <2 | 2-5 | 5-10 | >10 | | |
| 10* | 22 | 14 | 0 | 0 | 0 | 14 |
| 25* | 93 | 100 | 100 | 100 | 70 | 81 |
| 50* | 98 | 100 | 100 | 100 | 90 | 97 |
| 100** | 0 | 42 | 71 | 62 | 12 | 33 |
| 200** | 86 | 85 | 67 | 100 | 22 | 53 |

Remarks:
*Reserpine-ulcer
**Shay ulcer (Shay, H., Komarov, S.A., Fels, S.S., Meranze, D., Gruenstein, M., Siplet, H.: Gastroenterology 5, 45 /1945/)

In order to detect the possible atropine-like effects or side effects, the anticholinergic activity of the compounds was tested on mice, by the Pulewka method. The compounds were administered intraperitoneally, and the change in pupil diameter was measured. None of the tested compounds showed mydriatic effect.

The antidepressant activity was examined on mice, after oral administration. Tetrabenazine was administered to the animals in a dosage provoking maximum ptosis, and the inhibiting activity of the tested compounds was measured. The $ED_{50}$ values, calculated on the basis of these tests, are listed in Table 4.

Table 4

| Compound | Compound No. | ED₅₀ mg./kg. | LD₅₀ mg./kg | Therapeutical index |
| --- | --- | --- | --- | --- |
| 5,6-dimethoxyindazole-3-carboxylic acid-2'-hydroxy-benzylhydrazide | 32 | 22 | >3000 | 136.0 |
| 5,6-dimethoxyindazole-3-carboxylic acid-1'-(4''-nitrophenyl)-ethylhydrazide | 35 | 280 | >5000 | 17.9 |
| 5,6-dimethoxyindazole-3-carboxylic acid-benzylhydrazide | 30 | 140 | 2000 | 14.3 |
| amitryptiline* | — | 13 | 225 | 17.3 |

Remark:
*5-(3-dimethylamino-propylidene)-10,11-dihydro-5H-dibenzo(a,d)cycloheptane hydrochloride The therapeutical width of compound No. 32 significantly exceeds that of the well known agent, amitryptiline.

The invention is elucidated in detail by the aid of the following non-limiting Examples.

EXAMPLE 1

A mixture of 23.6 g. of 5,6-dimethoxyindazole-3-carboxylic acid hydrazide, 100 ml. of acetone and 5 ml. of acetic acid is refluxed for 2 hours under stirring. Upon cooling, 24 g. (87 %) of 5,6-dimethoxyindazole-3-carboxylic acid-isopropylidene hydrazide are separated; m.p.: 294°C.

EXAMPLE 2

A mixture of 23.6 g. of 5,6-dimethoxyindazole-3-carboxylic acid hydrazide, 11 g. of hexahydrobenzaldehyde and 300 ml. of ethanol is refluxed for 2 hours under stirring. Upon cooling, 26.3 g. (80 %) of 5,6-dimethoxyindazole-3-carboxylic acid-hexahydrobenzylidene hydrazide are separated; m.p.: 230°C.

EXAMPLE 3

A mixture of 50 g. of 5,6-dimethoxyindazole-3-carboxylic acid hydrazide, 20 g. of cyclohexanone and 300 ml. of methylcellosolve is refluxed under stirring, and the mixture is poured into 1000 ml. of methanol. Upon cooling, 56.2 g. (85 %) of 5,6-dimethoxyindazole-3-carboxylic acid-cyclohexylidene hydrazide are separated; m.p.: 290°C.

EXAMPLE 4

A mixture of 23.6 g. of 5,6-dimethoxyindazole-3-carboxylic acid hydrazide, 19 g. of N-benzyl-piperidone and 300 ml. of ethanol is refluxed for 3 hours. Upon cooling, 33 g. (81 %) of 5,6-dimethoxyindazole-3-carboxylic acid-(N'-benzylpiperylidene)-hydrazide are obtained; m.p.: 252°C.

EXAMPLE 5

5 ml. of concentrated sulfuric acid are added dropwise to the suspension of 6 g. of 5-nitrofurfurylidenediacetate in 100 ml. of ethanol, and the mixture is stirred for 10 to 30 minutes at 50°C. Thereafter a solution of 6 g. of 5,6-dimethoxyindazole-3-carboxylic acid hydrazide in 100 ml. of dimethylformamide is added, and the mixture is allowed to stand at room temperature for 24 hours. 6.3 g. (70 %) of 5,6-dimethoxyindazole-3-carboxylic acid-(5'-nitro-furfurylidene)-hydrazide are obtained; m.p.: 334°C. This compound is identical with Compund 26 of Table 5.

EXAMPLE 6

A solution of 12 g. of 5,6-dimethoxyindazole-3-carboxylic acid hydrazide in 50 ml. of acetaldehyde is stirred for 1 hour. The separated product is filtered off, washed with ether, and dried. The resulting 10.5 g. of 5,6-dimethoxyindazole-3-carboxylic acid-ethylidene hydrazide (m.p.: 155°C) are boiled for 4 hours in 100 ml. of isopropanol, in the presence of 2 g. of sodium borohydride. Thereafter the major part of isopropanol is evaporated, the residue is diluted with water, and 1 ml. of acetic acid and then 10 ml. of aqueous ammonia are added. The obtained mixture is extracted with chloroform, and the extract is evaporated. 11 g. (83 %) of viscous, oily 5,6-dimethoxyindazole-3-carboxylic acid-ethylhydrazide are otained.

EXAMPLE 7

3.7 g. of aluminium chloride are added to a stirred mixture of 8 g. of 5,6-dimethoxyindazole-3-carboxylic acid-isopropylidene hydrazide, prepared as described in Example 1, and 100 ml. of diethyleneglycol monomethylether at −10°C, under exclusion of atmospheric moisture. Thereafter a solution of 2 g. of sodium borohydride in diethylene glycol is added dropwise. The mixture is stirred for several hours at 0°C, the obtained solution is diluted with 1000 ml. of water, and the mixture is extracted with ethyl acetate. The organic phase is evaporated, and the product is recrystallized from ethanol. 5.2 g. (66 %) of 5,6-dimethoxyindazole-3-carboxylic acid-2'-propylhydrazide are obtained; m.p.: 177°C.

EXAMPLE 8

26 g. of 5,6-dimethoxyindazole-3-carboxylic acid hydrazide are reacted with a mixture of 30 ml. of diethylketone and 100 ml. of ethanol, as described in Example 1. The resulting 24.8 g. of product are stirred with 150 ml. of diethyleneglycol dimethylether at 0°C under exclusion of atmospheric moisture, and 18 g. of sodium borohydride are added to the mixture in small portions. Thereafter 20 ml. of a 48 % etheral solution of boron trifluoride is added dropwise to the mixture, and the obtained solution is stirred for further 1 to 2 hours at low temperature. The mixture is poured onto 500 g. of crushed ice in 50 ml. of concentrated hydrochloric acid. The reaction medium foams, and a viscous mass separates. It is extracted into chloroform, and the chloroform solution is processed in the usual way. The obtained crude product is recrystallized from ethanol. 20 g. (80 %) of 5,6-dimethoxyindazole-3-carboxylic acid-3'-pentylhydrazide are obtained; m.p.: 180° C.

EXAMPLE 9

13.9 g. of 5,6-dimethoxyindazole-3-carboxylic acid-cyclohexylidene hydrazide, prepared according to Example 3, are boiled for 2 hours in 200 ml. of isopropanol, in the presence of 3 g. of sodium borohydride. The mixture is evaporated, the residue is diluted with water, and the aqueous phase is extracted with chloroform. The chloroform solution is washed with water, dried, evaporated, and the residue is recrystallized from ethanol. 7.4 g. (53 %) of 5,6-dimethoxyindazole-3-carboxylic acid-cyclohexylhydrazide are otained; m.p.: 180°C.

EXAMPLE 10

A mixture of 4.6 g. of 5,6-dimethoxyindazole-3-carboxylic acid hydrazide and 3.4 g. of acetylnaphthalene is heated at 120° to 140°C for one hour. The mixture is cooled, and the solidified mass is washed with 100 ml. of hot methanol. A small sample isolated from the crude product and recrystallized from dimethylformamide melts at 290°C. The crude product is reacted as described in Example 8 to yield 3.5 g. (45 %) of 5,6-dimethoxyindazole-3-carboxylic acid-1'-(1''-naphthylethyl)-hydrazide, m.p.: 253°C.

5,6-Dimethoxyindazole-3-carboxylic acid hydrazide (a compound of the general formula /II/, wherein $R^1 = R^2 =$ methyl) is reacted with the reagents of the general formulae (III) or (IV) listed in Table 5 to yield the end-products listed in the same Table.

5,6-Diethoxyindazole-3-carboxylic acid hydrazide (a compound of the general formula /II/, wherein $R^1 = R^2 =$ ethyl) is reacted with the reagents of the general formulae (III) or (IV) listed in Table 6 to yield the end-products listed in the same Table

Table 5

| Compound No. | Reagent of the general formulae /III/ or /IV/ | Method /Example/ | Substituted hydrazide of the general formula /I/ | Yield % | M.p. °C |
|---|---|---|---|---|---|
| 11 | benzaldehyde | 2 | benzylidene- | 87 | 257 |
| 12 | salicylaldehyde | 2 | 2'-hydroxy-benzylidene- | 88 | 296 |
| 13 | 4-hydroxy-benzaldehyde | 2 | 4'-hydroxy-benzylidene- | 93 | 314 |
| 14 | 4-chloro-benzaldehyde | 2 | 4'-chloro-benzylidene- | 94 | 325 |
| 15 | 4-bromo-benzaldehyde | 2 | 4'-bromo-benzylidene- | 90 | 320 |
| 16 | piperonal | 2 | 3',4'-methylenedioxy-benzylidene- | 94 | 301 |
| 17 | 2-amino-benzaldehyde | 2 | 2'-amino-benzylidene- | 94 | 273 |
| 18 | 4-nitro-benzaldehyde | 2 | 4'-nitro-benzylidene- | 90 | 352 |
| 19 | 3,4,5-trimethoxybenzaldehyde | 2 | 3',4',5'-trimethoxy-benzylidene- | 95 | 289 |
| 20 | 1-naphthaldehyde | 2 | 1'-naphthylidene- | 96 | 294 |
| 21 | acetophenone | 2 | 1'-phenylethylidene- | 98 | 230 |
| 22 | 4-nitro-acetophenone | 2 | 1'-/4''-nitro-phenyl/-ethylidene | 99 | 318 |
| 23 | 4-methylmercapto-acetophenone | 2 | 1'-/4''-methylmercaptophenyl/-ethylidene | 97 | 226 |
| 24 | 3,4-dimethoxyphenyl-acetone | 2 | 1'-/3'',4''-dimethoxy-benzyl/-ethylidene- | 94 | 193 |
| 25 | furfurol | 2 | furfurylidene- | 92 | 268 |
| 26 | 5-nitro-furfurol | 2 | 5'-nitro-furfurylidene- | 74 | 334 |
| 27 | hexahydrobenzaldehyde | 1 to 9 | cyclohexylmethyl- | 58 | 174 |
| 28 | cycloheptanone | 1 to 9 | cycloheptyl- | 60 | 210 |
| 29 | cyclododecanone | 1 to 9 | cyclododecyl- | 61 | 155 |
| 30 | benzaldehyde | 1 to 9 | benzyl- | 90 | 190 |
| 31 | acetophenone | 1 to 9 | 1'-phenylethyl- | 65 | 210 |
| 32 | salicylaldehyde | 1 to 9 | 2'-hydroxy-benzyl- | 62 | 202 |
| 33 | 4-hydroxy-benzaldehyde | 1 to 9 | 4'-hydroxy-benzyl- | 45 | 205 |
| 34 | 4-dimethylamino-benzaldehyde | 1 to 9 | 4'-dimethylamino-benzyl-/HCl salt/ | | |
| 35 | 4-nitro-acetophenone | 1 to 9 | 1'-/4''-nitro-phenyl/-ethyl- | 80 | 204 |
| 36 | 4-methylmercapto-acetophenone | 1 to 9 | 1'-/4''-methylmercaptophenyl/-ethyl- | 40 | 192 |
| 37 | 3,4-dimethoxyphenyl-acetone | 1 to 9 | 2'-[3'-/3'',4''-dimethoxyphenyl]-propyl- | 48 | 180 |
| 38 | 3,4,5-trimethoxybenzaldehyde | 1 to 9 | 3',4',5'-trimethoxybenzyl- | 73 | 180 |
| 39 | 2,4,5-trimethoxybenzaldehyde | 1 to 9 | 2',4',5'-trimethoxybenzyl- | 72 | 218 |
| 40 | 3-benzyloxy-4-methoxy-benzaldehyde | 1 to 9 | 3'-benzyloxy-4'-methoxy-benzyl- | 40 | 158 |
| 41 | 4-benzyloxy-propiophenone | 1 to 9 | 1'-/4''-benzyloxyphenyl/-propyl- | 80 | 180 |
| 42 | 1-naphthaldehyde | 1 to 9 | 1-naphthyl-methyl- | 53 | 243 |
| 43 | palmitophenone | 1 to 9 | 1'-phenyl-hexadecyl- | 90 | 110 |
| 44 | benzyl-ethyl-ketone | 1 to 9 | 2'-/1''-phenyl/-butyl- | 76 | 148 |
| 45 | 1-methyl-piperidone-4 | 1 to 9 | 4'-/1''-methyl-piperidyl/- | 65 | 142 |
| 46 | 4-chloro-benzaldehyde | 1 to 9 | 4'-chlorobenzyl- | 66 | 198 |

Table 6

| Compound No. | Reagent of the general formulae /III/ or /IV/ | Method /Example/ | Substituted hydrazide of the general formula /I/ | Yield % | m.p. °C |
|---|---|---|---|---|---|
| 47 | acetone | 1 to 10 | isopropyl- | 72 | 204 |
| 48 | benzaldehyde | 1 to 10 | benzyl- | 72 | 140 |
| 49 | 2-chlorobenzaldehyde | 1 to 10 | 2'-chlorobenzyl- | 37 | oil |
| 50 | benzyl-ethyl-ketone | 1 to 10 | 2'-/1''-phenyl/-butyl- | 50 | 147 |

What we claim is:
1. A compound of the formula (I)

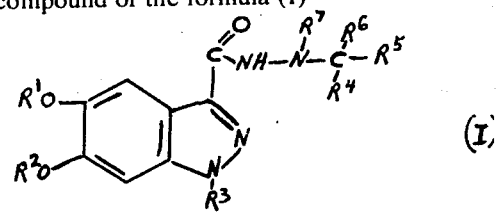

wherein one of $R^4$ and $R^5$ is hydrogen and the other is phenyl, substituted phenyl, phenylalkyl or substituted phenylalkyl, wherein said substituted phenyl groups contain 1 to 3 alkyl, $C_{1-3}$ alkoxy, hydroxyl benzyloxy, nitro, amino, lower alkylamino, di-lower alkylamino, methylenedioxy, alkyl-mercapto, alkylsulfonyl or halogen substituents, $R^1$ and $R^2$ are always the same and represent a $C_{1-4}$ alkyl group, $R^3$ is hydrogen and $R^6$ and $R^7$ are hydrogen or $R^6$ and $R^7$ form together a valence bond; or a pharmaceutically acceptable salt thereof.

2. The compound according to claim 1 wherein one of $R^4$ and $R^5$ is hydrogen and the other is phenylalkyl or substituted phenylalkyl.

3. The compound according to claim 1 wherein $R^4$ is hydrogen and $R^5$ is phenyl, substituted phenyl, phenylalkyl or substituted phenylalkyl.

4. The compound according to claim 1 wherein said compound is 5,6-dimethoxyindazole-3-carboxylic acid-2'-hydroxy-benzylhydrazide.

* * * * *